United States Patent [19]

Vianen et al.

[11] Patent Number: 5,945,110
[45] Date of Patent: Aug. 31, 1999

[54] COMPOSITION FOR THE PREVENTION OR TREATMENT OF NAPPY RASH

[75] Inventors: Gerardus Maria Vianen; Pieter Diederick Meyer, both of Roosendaal; Jacobus Petrus Maria Bink, Etten-Leur; Bastiaan Willem Walraven, Roosendaal, all of Netherlands

[73] Assignee: Cooperatie Cosun U.A., Netherlands

[21] Appl. No.: 08/889,118

[22] Filed: Jul. 7, 1997

[30] Foreign Application Priority Data

Jul. 5, 1996 [NL] Netherlands ............................ 1003524

[51] Int. Cl.$^6$ ............................... A61K 6/00; A61K 7/00; A01N 25/34
[52] U.S. Cl. ............................................. 424/401; 424/402
[58] Field of Search ....................... 106/156.24; 424/401, 424/402, 78.06; 514/865

[56] References Cited

U.S. PATENT DOCUMENTS

| | | | |
|---|---|---|---|
| 4,778,881 | 10/1988 | Nieuwenhuis et al. | 536/119 |
| 5,231,087 | 7/1993 | Thornfeldt . | |
| 5,362,488 | 11/1994 | Sibley et al. . | |

FOREIGN PATENT DOCUMENTS

| | | | |
|---|---|---|---|
| 2274877 | 9/1978 | Australia | A61K 31/23 |
| 0117613 | 9/1984 | European Pat. Off. | A61L 15/00 |
| 0311344 | 4/1989 | European Pat. Off. | A61L 15/00 |
| 0613675 | 9/1994 | European Pat. Off. | A61K 7/00 |
| 0750903 | 1/1997 | European Pat. Off. | A61K 7/32 |
| 9616681 | 6/1996 | WIPO | A61L 15/26 |

OTHER PUBLICATIONS

Patent Abstracts of Japan, vol. 14, No. 86 (C–690) & JP 01 299233 A (Dai Ichi Kogyo Seiyaku Co., Ltd.) "Remedy of Skin Wound".

STN File Supplier, Karlsruhe, DE, File XP002027636, Chemical Abstract, vol. 117, No. 21939.

Takahashi, Kenji, et al., "Bactericides containing glucose fatty acid esters for gram–positive bacteria and bacterial control with them."

Database WPI, Section Ch, Week 7707, Derwent Publications, Ltd., London, GB; D21, AN 77–11980 XP002027637 & JP 52 000 806 A, Daiichi Kogyo KK, Jan. 6, 1977, "Sugar ester of wool fatty acid preparation giving good antibacterial, emulsifying and dispersing properties, for use in ointments and creams."

Balsam, M. S. et al., Cosmetics Science and Technology, Second Edition, vol. 1, pp. 128–131.

Harry, Ralph G., "Harry's Cosmeticology," Sixth Edition, The Principles and Practice of Modern Cosmetics, vol. 1, pp. 540–543.

Leyden, James J. M.D., "Diaper Dermatitis," Dermatologic Clinics, vol. 4, No. 1, Jan. 1986, pp. 23–28.

*Primary Examiner*—Thurman K. Page
*Assistant Examiner*—Sharon Howard
*Attorney, Agent, or Firm*—Webb Ziesenheim Logsdon Orkin & Hanson, P.C.

[57] ABSTRACT

The invention relates to compositions and products based on fabric, such as baby tissues, and based on composite materials, such as disposable nappies, which compositions and products are suitable for the prevention or treatment of nappy rash and nappy dermatitis. The active antimicrobial substances used according to the invention are one or more sugar fatty acid esters, the monoester content of which must be at least 30%. The fatty acid component of the active substances is formed by one or more, saturated or unsaturated fatty acids having 6–22 carbon atoms, which fatty acids are straight-chain or branched and also can contain one or more hydroxyl groups. The sugar component of the active substances is, for example, sucrose, glucose, fructose, sorbitol or a mixture thereof. The abovementioned active substances, which are completely harmless, are used in an amount of 0.01–15% by weight in the composition or the product.

17 Claims, No Drawings

COMPOSITION FOR THE PREVENTION OR TREATMENT OF NAPPY RASH

The invention relates to compositions and products based on fabric, such as baby tissues, and based on composite materials, such as disposable nappies, which compositions and products are suitable for the prevention or treatment of nappy rash.

One of the most common skin problems in babies and toddlers relates to nappy rash, which is also termed nappy dermatitis. The studies cited in U.S. Pat. No. 5,362,488, which were carried out on children younger than 2 years old, revealed that approximately two-thirds of the children were suffering from some form of nappy rash. For about 10% of the children the nappy rash was rated as moderate, whilst for 5% of the children the nappy rash was recorded as severe.

Up to now the urine and the faeces of the children have been regarded as the main causes of the development of nappy rash. According to U.S. Pat. No. 5,362,488, faeces must be regarded as the main cause of nappy rash since nappy rash apparently occurs more frequently in the presence of faeces than in the presence of urine. Furthermore, it is reported in U.S. Pat. No. 5,362,488 that nappy rash renders a child susceptible to irritation and infection, the two most common types of infection being related to yeasts and bacteria. The most common yeast infection is apparently caused by *Candida albicans* and the most common bacterial infection by *Staphylococcus aureus*. A similar combination of infections is also indicated in other literature. For example, the influential role of *Corynebacterium ammoniagenes* and *Staphylococcus aureus* on nappy rash is described in Barnett G., Baby Toiletries, Cosmetic Science and Technology, second edition, vol. 1, pp. 128–131, in Harry R., Harry's Cosmeticology, Principles and Practice of Modern Cosmetics, 6th edition, vol. 1, pp. 540–542 and in Leyden J., Diaper Dermatitis, Dermatological Clinics, 1986, vol. 4, no. 1, pp. 23–28, whilst in Leyden J., (loc. cit.) an infection with *Candida albicans* is reported as a secondary effect.

U.S. Pat. No. 5,362,488 proposes a buffered skin cream, which contains, inter alia, methylparaben and propylparaben as antimicrobial agents, for the prevention and treatment of nappy rash. However, it has been found that parabens are substances which are not harmless to man since these substances can lead to sensitisation. This sensitisation is expressed, inter alia, in chronic dermatitis, angio-oedema, hyperactivity, asthma, eczema and loss of sensation in the oral cavity. Furthermore, parabens are powerful histamine liberators (see E=eetbaar (E=edible), Dr. J. Kamsteeg & Ir. N.I.A. Baas, 3rd impression, Becht, Haarlem).

EP-A 0 613 675 describes cleaning cloths or tissues which contain an antimicrobial emulsion of low viscosity, which is suitable for controlling causative microorganisms in nappy rash. In addition to one or more bacterial preservatives such as parabens and chlorine-containing substances, such as 5-chloro-2-methyl-4-isothiazolin-3-one, the only specific antimicrobial agent mentioned is the compound cetylpyridinium chloride. This antimicrobial agent, which is said to act against microorganisms which play a role in nappy rash, such as Staphylococcus species and *Candida albicans,* cannot be regarded as harmless since quaternary ammonium compounds, such as said cetylpyridinium chloride, are not permitted as preservatives in the food industry (no E number).

Furthermore, disposable nappies which, in addition to a top layer and a backing, also contain a core layer, which core layer contains an antimicrobial agent in addition to an acid buffer, are described in EP-A 0 311 344. Once again, quaternary ammonium salts, such as the abovementioned cetylpyridinium chloride, are mentioned, inter alia, as examples of such an antimicrobial agent.

The aim of the invention is, firstly, to develop a composition which can be used to prevent or treat nappy rash and nappy dermatitis, which composition contains a substance harmless to man as antimicrobial agent.

Surprisingly, the abovementioned aim can be achieved if one or more sugar fatty acid esters are used as antimicrobial agent. This result is the more surprising in view of the fact that the sugar fatty acid esters concerned—certainly in lower concentrations—display no or virtually no action against other, skin-friendly, microorganisms belonging to the skin flora of man, such as *Micrococcus luteus* and *Staphylococcus epidermis*.

The invention therefore firstly relates to a composition for the prevention or treatment of nappy rash, which is characterised in that at least one or more sugar fatty acid esters are present therein as active antimicrobial substance.

The sugar fatty esters to be used as active substance in the compositions according to the invention can be prepared on the basis of a sugar such as sucrose, glycose, fructose or galactose or of a polyol such as sorbitol, mannitol, lactitol or xylitol, or of a mixture thereof, on the one hand, and saturated or unsaturated fatty acids having 6–22 carbon atoms, which fatty acids can be straight-chain or branched, on the other hand. Furthermore, the fatty acids can also contain one or more hydroxyl groups. Examples of suitable fatty acids are lauric acid, myristic acid, palmitic acid, stearic acid, oleic acid, hydroxy- and isostearic acid. A method of preparation for suitable sugar fatty acid esters is described, inter alia, in U.S. Pat. No. 4,778,881. Suitable sugar fatty acid esters can also be prepared by hydrolysis of such products. Specifically, hydrolysis of, for example, sucrose fatty acid ester leads to the formation of (a mixture of) glucose fatty acid esters and fructose fatty acid esters.

The sugar fatty acid esters in the compositions according to the invention must have a monoester content of at least 30%, advantageously of over 50% and more particularly of at least 70%. In the case of 30% monoesters, it can be stated that usually 40–70% diesters and 0–30% tri- or higher esters are also present in the sugar fatty acid ester product. The fatty acid component used in these esters can be one or more of, for example, the abovementioned fatty acids, such as the combination laurate/palmitate, laurate/stearate or palmitate/stearate.

The sugar fatty acid esters are mild and non-irritant to human skin. Said esters are non-toxic, odourless and, under the conditions for use, unsusceptible or barely susceptible to hydrolysis. Furthermore, the sugar fatty acid esters can be regarded as harmless since, under the conditions for use, said esters—as far as is known—develop no action whatsoever which is harmful to man.

In the ready-to-use compositions, depending on the form thereof, the sugar fatty acid esters can be used in a wide range, for example in a range of 0.01–15% by weight, advantageously 0.1–10% by weight, and very particularly 0.1–5% by weight, calculated on the basis of the total weight of the composition.

The compositions according to the invention can be produced in diverse forms, such as soaps, creams, lotions, sticks and the like.

Products based on fabric or based on composite materials also fall within the scope of the invention. In the context of the invention, fabric is understood to be woven or nonwoven material. Examples of fabric are materials based on textiles, such as cotton, for example cotton nappies, based on cellulose-containing material, such as paper, for example tissue paper, and based on synthetic fibres, which are used as the base material for, in particular, disposable nappies. The active substances according to the invention can be incorporated or impregnated in the fabric as such or in the form of, for example, an emulsion. Examples of composite materials which may be mentioned in this context are, inter alia, disposable nappies, which in general are made up of a top layer, a backing and an intermediate layer, in which intermediate layer the active substances according to the invention are usually incorporated.

In addition to the active antimicrobial sugar fatty acid esters, the compositions and products according to the invention can also contain—depending on the embodiment—the active or non-active materials known from the prior art, such as buffers, cleansing agents, surface-active substances, emulsifiers and perfumes, as well as other active substances, such as lipase and protease inhibitors; see, for example, EP-A 0 117 613.

The invention is explained in more detail with the aid of the following example, which must not be interpreted as being restricting.

EXAMPLE

MATERIAL AND METHOD

Harmful Strains

| | |
|---|---|
| Corynebacterium ammoniagenes | ATCC* 6871 |
| Staphylococcus aureus | ATCC 25923 |
| Candida albicans | ATCC 14053 |

(*ATCC = American Type Culture Collection, Maryland 20852, USA)

These strains were cultured in, respectively, Nutrient Broth (NB, Oxoid CM 1), Trypton Soya Broth (TSB, Oxoid CM 129) and YM Broth (Yeast, Malt, Peptone and Glucose—Difco 0711-170) and incubated at, respectively, 30, 37 and 30° C. After checking for purity, they were frozen in liquid nitrogen (20% glycerol).

NB plus 0.5% glucose (NBglc) and Nutrient Agar (Oxoid CM 3) plus 0.5% glucose (NAglc) was used as common medium for the three strains.

Skin-Friendly Strains:

| | |
|---|---|
| Micrococcus luteus | ATCC 533 |
| Staphylococcus epidermis | ATCC 155. |

The *Micrococcus luteus* strain was incubated at 30° C. and the *Staphylococcus epidermis* strain at 37° C. on TSB (Trypton Soya Broth: Oxoid CM 129). The two strains were tested for purity and then frozen in glycerol (20% ) in liquid nitrogen. In addition, the strains were kept on plate (TSBA medium; TSBA=Trypton Soya Broth (medium CM 129 from Oxoid Ltd)+1% agar) and further inoculated at regular intervals (at least once per week).

Sugar Fatty Acid Esters:

Sisterna® SP70=70% stearate, 30% palmitate–70% sucrose monoester. Sisterna® L70=70% laurate, 30% palmitate–70% sucrose monoester.

For the harmful strains these sugar fatty acid esters were added to the NAglc medium in concentrations of 0, 400, 800, 1600 and 3200 mg/l (prepare highest concentration first and then dilute successively with NAglc medium) before sterilisation. After sterilisation (15 minutes at 120° C.) plates were poured therefrom, which plates were used to test the inhibitory action of these sugar fatty acid esters on the abovementioned strains.

For the skin-friendly strains the sucrose fatty acid esters were added to the TSBA medium in the abovementioned concentrations before sterilisation, after which the mixtures were sterilised for 15 minutes at 120° C. The plate which was provided with a TSBA medium was then inoculated with 100 µl culture and incubated at the desired temperature (see above). For this purpose use was made of overnight cultures in TSB (=Trypton Soya Broth), which were inoculated undiluted (o.n.) and diluted 1:100.

Test Method

The test method used was the plate method. With this method the NAglc medium or the TSBA medium, as appropriate, was made up with the sucrose fatty acid ester solutions having the abovementioned concentrations. The abovementioned sugar fatty acid ester-NAglc plates were inoculated with 100 µl of the 1:50 dilution of overnight culture of the said harmful strains in the NBglc medium. The abovementioned TSBA plates were inoculated with 100 µl of undiluted overnight culture in TSB and 100 µl of a 1:100 dilution of overnight culture in TSB (Trypton Soya Broth= Oxoid CM 129) of the skin-friendly strains. The plates with *Corynebacterium ammoniagenes* and *Candida albicans* or *Micrococcus luteus* were then incubated at a temperature of 30° C. and the plates with *Staphylococcus aureus* or *Staphylococcus epidermis* at a temperature of 37° C. for 20–28 hours, after which the inhibition was assessed.

The inhibition obtained was related to the growth in the positive controls. The inhibition was categorised as 0, 0 to 20, 20 to 40, 40 to 60, 60 to 80 and 80 to 100% inhibition.

The control used for the harmful strains was a blank determination in an NAglc medium without sucrose fatty acid ester solution.

The control used for the skin-friendly strains was a blank determination in a TSBA medium without sucrose fatty acid ester solution.

The results of the tests are given in table A below.

TABLE A

| | | C. ammoniagenes | S. aureus | C. albicans | M. luteus | | S. epidermis | |
|---|---|---|---|---|---|---|---|---|
| Ester: conc. (ppm) | | 1:50 | 1:50 | 1:50 | o.n. | 1:100 | o.n. | 1:100 |
| SP70 | 400 | +++++ | +++ | 0 | 0 | + | 0 | 0 |
| | 800 | +++++ | +++ | 0 | +++ | +++++ | 0 | 0 |
| | 1600 | +++++ | ++++ | 0 | ++++ | +++++ | 0 | 0 |
| | 3200 | +++++ | ++++ | 0 | ++++ | +++++ | 0 | 0 |
| L70 | 400 | +++++ | ++ | +++ | 0 | 0 | 0 | 0 |
| | 800 | +++++ | ++ | +++ | 0 | 0 | 0 | 0 |
| | 1600 | +++++ | +++ | ++ | 0 | + | 0 | 0 |
| | 3200 | +++++ | ++++ | ++++ | + | + | 0 | 0 |
| Control | 0 | 0 | 0 | 0 | 0 | 0 | 0 | 0 |

Legend:
0 = no inhibition,
+ = 0–20% inhibition,
++ = 20–40% inhibition,
+++ = 40–60% inhibition,
++++ = 60–80% inhibition, TABLE A-continued

| | C. ammoniagenes | S. aureus | C. albicans | M. luteus | | S. epidermis | |
|---|---|---|---|---|---|---|---|
| Ester: conc. (ppm) | 1:50 | 1:50 | 1:50 | o.n. | 1:100 | o.n. | 1:100 |

+++++ = 80–100% inhibition, with respect to control
SP70 = 70% stearate, 30% palmitate - 70% sucrose monoester
L70 = 70% laurate, 30% palmitate - 70% sucrose monoester

We claim:

1. Composition for inhibiting growth of nappy rash bacteria, comprising a sugar fatty acid ester and one of an active and a non-active material, wherein the fatty acid component of the sugar fatty acid ester has 12–18 carbon atoms, the monoester content of the sugar fatty acid ester is at least 70% and the composition is about 200 to 50,000 ppm sugar fatty acid ester.

2. Composition according to claim 1, wherein the fatty acid component contains one or more hydroxyl groups.

3. Composition according to claim 1, wherein the fatty acid component of the active substance is selected from the group consisting of lauric acid, myristic acid, palmitic acid, stearic acid, oleic acid, hydroxy- and/or isostearic acid and a mixture thereof.

4. Composition according to claim 1, wherein the sugar component of the active substance is selected from the group consisting of sucrose, glucose, fructose, galactose, sorbitol, mannitol, lactitol, xylitol and a mixture thereof.

5. A product for inhibiting growth of nappy rash bacteria comprising a fabric material impregnated with the composition of claim 1.

6. Method for inhibiting growth of nappy rash bacteria comprising applying to skin a composition containing 200 ppm to 50,000 ppm of a sugar fatty acid ester wherein the fatty acid component of the sugar fatty acid ester has 12–18 carbon atoms and the monoester content of the sugar fatty acid ester is at least 70%.

7. Method as claimed in claim 6, wherein the fatty acid component of the sugar fatty acid ester is selected from the group consisting of lauric acid, myristic acid, palmitic acid, stearic acid, oleic acid, hydroxy- or isostearic acid and a mixture thereof.

8. Method as claimed in claim 6, wherein the sugar component of the sugar fatty acid ester is selected from the group consisting of sucrose, glucose, fructose, galactose, sorbitol, mannitol, lactitol, xylitol and a mixture thereof.

9. Method as claimed in claim 6, wherein the fatty acid component of the sugar fatty acid ester is about 20%–70% stearate or laurate and about 30%–80% palmitate.

10. Method as claimed in claim 9, wherein the fatty acid component of the sugar fatty acid ester is about 20% stearate and about 80% palmitate and the sugar fatty acid ester is about 75% monoester.

11. Method as claimed in claim 6, wherein the fatty acid component of the sugar fatty acid ester is about 70% laurate or stearate and about 30% palmitate and is about 70% monoester.

12. Method as claimed in claim 6, wherein the composition is impregnated in a fabric.

13. Method as claimed in claim 6, wherein the fatty acid component of the sugar fatty acid ester is hydroxylated.

14. Composition for inhibiting growth of nappy rash bacteria as claimed in claim 1, containing a sugar fatty acid ester of about 20%–70% stearate or laurate and about 30%–80% palmitate.

15. Composition of claim 14, wherein the sugar fatty acid ester is a sucrose fatty acid ester.

16. Composition of claim 14, wherein the sugar fatty acid ester is about 80% palmitate and about 20% stearate and wherein the sugar fatty acid ester is about 75% monoester.

17. Composition of claim 16, wherein the sugar fatty acid ester is about 70% laurate or stearate and about 30% palmitate and wherein the sugar fatty acid ester is about 70% monoester.

* * * * *